United States Patent
Su et al.

(10) Patent No.: US 7,410,763 B2
(45) Date of Patent: Aug. 12, 2008

(54) MULTIPLEX DATA COLLECTION AND ANALYSIS IN BIOANALYTE DETECTION

(75) Inventors: Xing Su, Cupertino, CA (US); Lei Sun, Santa Clara, CA (US); Mineo Yamakawa, Campbell, CA (US); Jingwu Zhang, San Jose, CA (US); Qing Ma, Santa Clara, CA (US); Tae-Woong Koo, Cupertino, CA (US); Richard Jones, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 55 days.

(21) Appl. No.: 11/216,112

(22) Filed: Sep. 1, 2005

(65) Prior Publication Data

US 2007/0048746 A1    Mar. 1, 2007

(51) Int. Cl.
 *C12Q 1/68* (2006.01)
 *G01N 33/53* (2006.01)
 *C12M 1/00* (2006.01)

(52) U.S. Cl. ................... 435/6; 435/7.1; 435/283.1; 435/287.2

(58) Field of Classification Search ............... 435/6, 435/287.2, 7.1, 283.1
See application file for complete search history.

(56) References Cited

U.S. PATENT DOCUMENTS

| | | | |
|---|---|---|---|
| 4,245,171 A * | 1/1981 | Rabinowitz et al. ......... 359/327 |
| 4,444,879 A | 4/1984 | Foster et al. |
| 5,766,963 A | 6/1998 | Baldwin et al. |
| 6,514,767 B1 | 2/2003 | Natan |
| 6,861,263 B2 | 3/2005 | Natan |
| 2002/0090662 A1 | 7/2002 | Ralph |
| 2003/0032035 A1* | 2/2003 | Chatelain et al. ................ 435/6 |
| 2003/0224457 A1* | 12/2003 | Hurt et al. ..................... 435/7.2 |
| 2004/0053237 A1* | 3/2004 | Liu et al. ........................ 435/6 |
| 2004/0142484 A1* | 7/2004 | Berlin et al. ................. 436/171 |
| 2004/0152200 A1* | 8/2004 | Deshmukh ..................... 436/86 |
| 2005/0064435 A1 | 3/2005 | Su et al. |
| 2005/0064604 A1 | 3/2005 | Bohmann et al. |
| 2005/0123974 A1 | 6/2005 | Gilmanshin et al. |
| 2005/0130163 A1 | 6/2005 | Smith et al. |
| 2005/0147976 A1 | 7/2005 | Su |
| 2005/0147977 A1* | 7/2005 | Koo et al. ....................... 435/6 |
| 2005/0151966 A1* | 7/2005 | Packirisamy et al. ......... 356/328 |
| 2005/0196876 A1* | 9/2005 | Chan et al. ................... 436/518 |
| 2006/0057576 A1* | 3/2006 | Paszkowski et al. ............ 435/6 |
| 2007/0117212 A1* | 5/2007 | Kautz et al. .................. 436/137 |

OTHER PUBLICATIONS

Su et al., Composite Organic-Inorganic Nanoparticles (COINs) with chemically encoded optical signatures. □□NANO Letters 5(1) : 49-54 (Jan. 2005).*
Wang et al., Microarrays assembled in microfluidic chips fabricated from poly(methyl methacrylate) for the detection of low-abundant DNA mutations. Analytical Chemistry 75 : 1130-1140(2003).*
Han, et al., "Quantum-Dot-Tagged Microbeads for Multiplexed Optical Coding of Biomolecules", Nature Biotechnology, vol. 19, Jul. 2001 (pp. 631-635).
Non-Final Office Action (mailed Jul. 2, 2007), U.S. Appl. No. 11/026,857, filed Dec. 30, 2004, First Named Inventor: Xing Su (30 pages).
Non-Final Office Action (mailed Jun. 29, 2007), U.S. Appl. No. 11/027,470, filed Dec. 30, 2004, First Named Inventor: Mark Roth (25 pages).

* cited by examiner

*Primary Examiner*—Ethan Whisenant
(74) *Attorney, Agent, or Firm*—Darby & Darby PC

(57) ABSTRACT

Method and device to collect multiplex data simultaneously in analyte detection and analyze the data by experimentally trained software (machine-learning) is disclosed. Various ways (magnetic particles and microcoils) are disclosed to collect multiple reporter (tag) signals. Multiplex detection can increase the biomolecule analysis efficiency by using small sample size and saving assay reagents and time. Machine learning and data analysis schemes are also disclosed. Multiple affinity binding partners, each labeled by a unique reporter, are contacted with a sample and a green spectrum is taken to detect multiple reporter signals. The spectrum is deconvoluted by experimentally trained software to identify multiple analytes.

21 Claims, 9 Drawing Sheets

FIG. 1
Methods to create sub-set of binding complexes
A: 2 reporter method
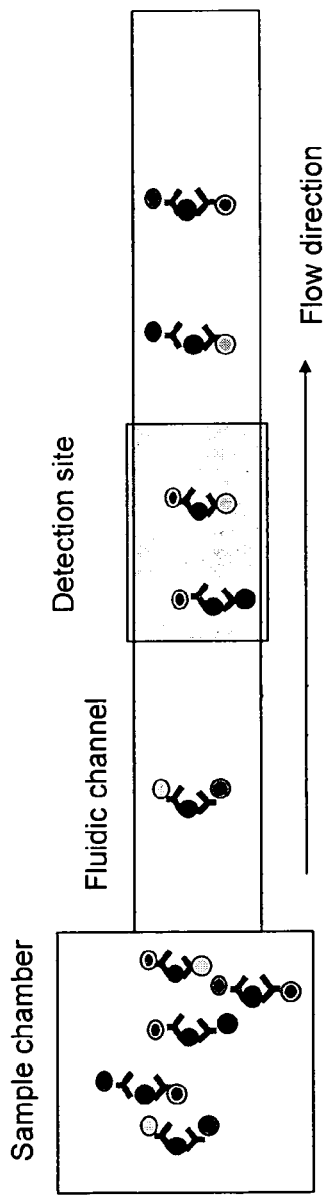
B: spatial position and reporter method
Antibodies are grouped, immobilized on isolated sub-surface in an enclosed chip
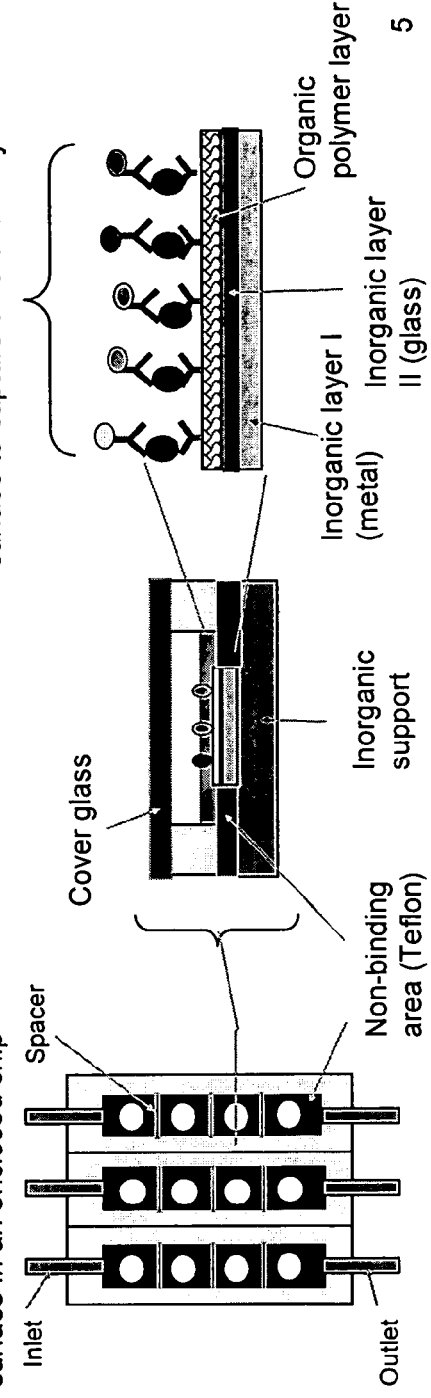

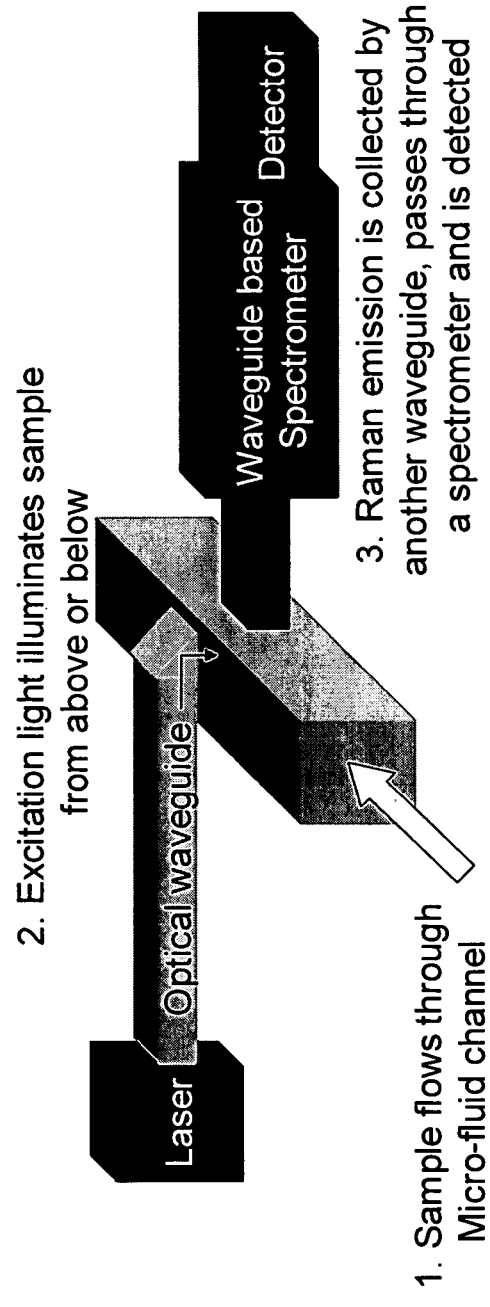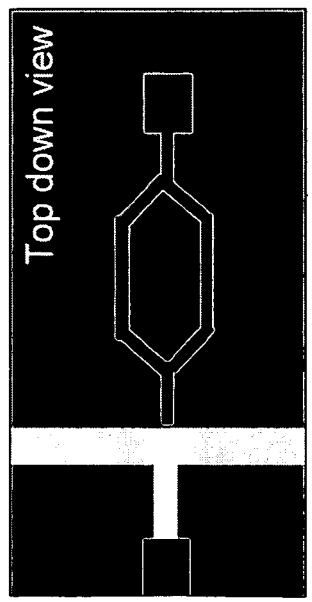
FIG. 3

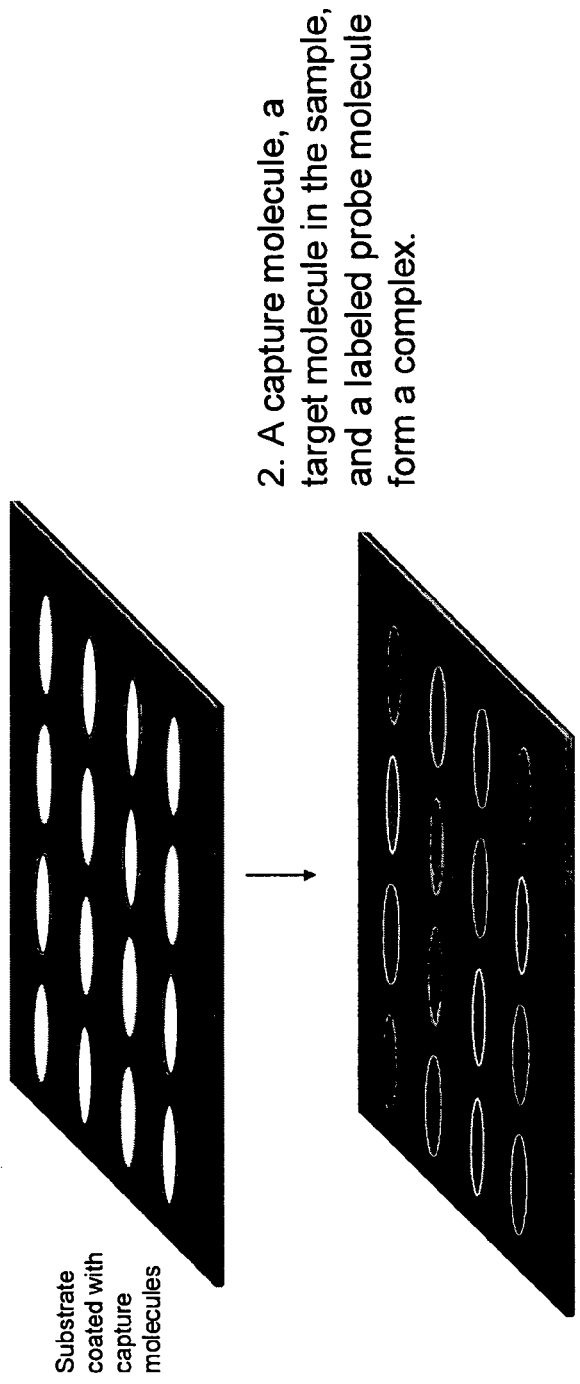

FIG. 4

Raman-on-chip
Specific embodiment
2. micro-array based system, sample prep

1. On a substrate coated with capture molecules, introduce the sample and the labeled probe molecules.

2. A capture molecule, a target molecule in the sample, and a labeled probe molecule form a complex.

Probe molecules with COIN label

Target molecules in the sample

Substrate coated with capture molecules

FIG. 8
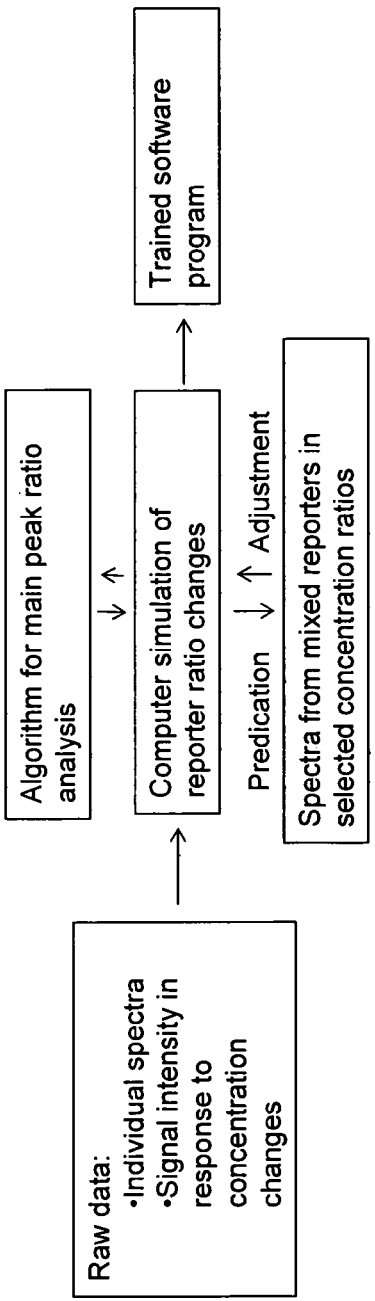
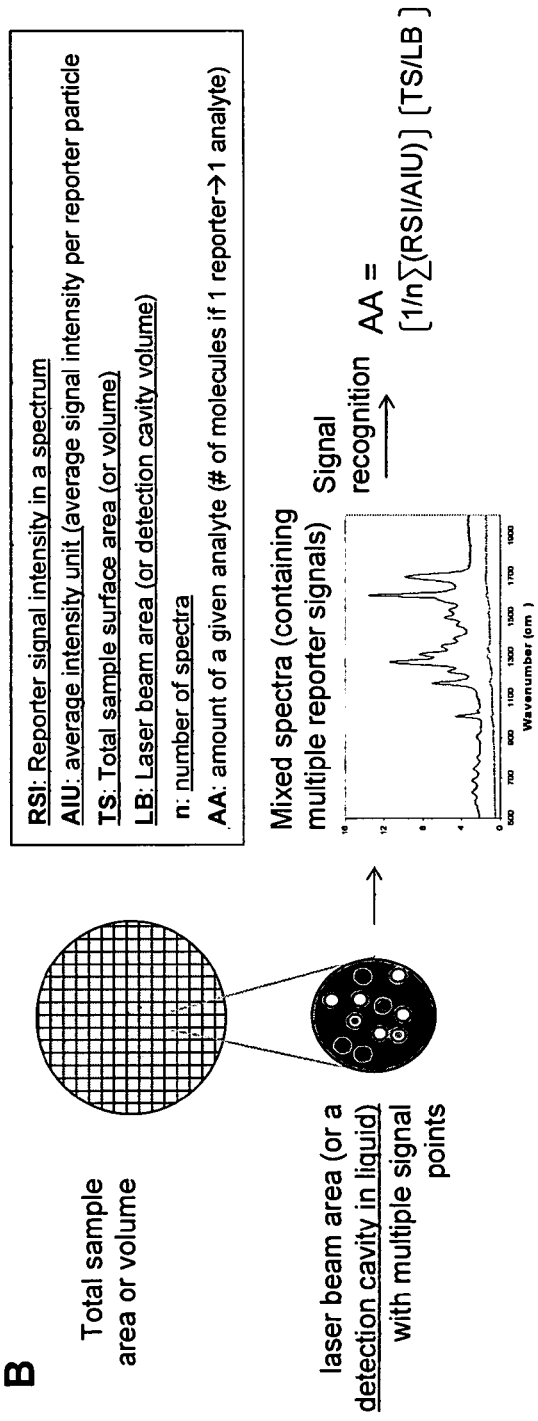

MULTIPLEX DATA COLLECTION AND ANALYSIS IN BIOANALYTE DETECTION

RELATED APPLICATIONS

This application is related to U.S. patent application Ser. No. 10/748,336, filed Dec. 29, 2003, entitled "Composite Organic-Inorganic Nanoparticles (COIN) as SERS Tags for Analyte Detection," U.S. patent application Ser. No. 10/916,710, filed Aug. 11, 2004, entitled "Multiplex Detection of Analytes in Fluid Systems," U.S. patent application Ser. No. 10/927,996, filed Aug. 26, 2004, entitled "Biomolecule Analysis Using Raman Surface Scanning", and U.S. patent application Ser. No. 11/027,470, filed Dec. 30, 2004, entitled "Biomolecule Analysis Using Raman Surface Scanning."

FIELD OF INVENTION

The embodiments of the invention relate to methods and devices for complex data collection and analysis in multiplexed biomolecule detection. The invention transcends several scientific disciplines such as polymer chemistry, biochemistry, molecular biology, medicine and medical diagnostics.

BACKGROUND

The molecular-level origins of disease are being elucidated at a rapid pace, potentially ushering in a new era of personalized medicine in which a specific course of therapy is developed for each patient. To fully exploit this expanding knowledge of disease phenotype, new methods for detecting multiple biomolecules (e.g., DNA and proteins) simultaneously are required. The multiplex biomolecule detection methods must be rapid, sensitive, highly parallel, and ideally capable of diagnosing cellular phenotype in vivo.

Some biomolecule detection methods have been developed based upon the unique electrochemical and photoelectrochemical properties of metal particles. In one assay method, gold nanoparticles (10 nm diameter) are tagged with ssDNA probe strands and a photoactive dye molecule. A metal electrode of a microarray chip (also called gene chip) is also modified with ssDNA probe strands. If a target (the analyte or bioanalyte) mRNA or ssDNA is complementary to the probe on the particle and the substrate, hybridization will occur which brings the particle in contact with the electrode. A laser is then rastered across the surface. When the laser addresses a spot in which nanoparticles are bound, the dye molecule is electronically excited, and the excited electron is injected into the electrode. The electron is collected as a current, signifying the presence of a particular DNA analyte.

Synthesis of a functionalized electrode having polymer arrays on an electrode of a microarray chip is known. Examples of such polymer arrays include nucleic acid arrays, peptide arrays, and carbohydrate arrays.

One method of preparing functionalized electrodes of polymer arrays on microarray chips involves photolithographic techniques using photocleavable protecting groups. Briefly, the method includes attaching photoreactive groups to the surface of a substrate, exposing selected regions of the substrate to light to activate those regions, attaching a monomer with a photoremovable group to the activated regions, and repeating the steps of activation and attachment until macromolecules of a length and sequence are synthesized.

Additional methods and techniques applicable to prepare a functionalized electrode include electrochemical synthesis. One example includes providing a porous substrate with an electrode therein, placing a molecule having a protected chemical group in proximity of the porous substrate, placing a buffering solution in contact with the electrode and the porous substrate to prevent electrochemically generated reagents from leaving the locality of the electrode (the use of confinement electrodes to prevent reagents from diffusing away have also been described), applying a potential to the electrode to generate electrochemical reagents capable of deprotecting the protected chemical functional group of the molecule, attaching the deprotected chemical functional group to the porous substrate or a molecule on the substrate, and repeating the above steps until polymers of a length and sequence are synthesized.

The biomolecules on microarray chip typically are detected through optical readout of fluorescent labels attached to a target molecule that is specifically attached or hybridized to a probe molecule. These optical methods are difficult to implement and miniaturize because they rely on the use of optical labels and require large or expensive instrumentation.

BRIEF DESCRIPTION OF THE DRAWINGS

FIG. 1 shows a schematic of the methods and devices to create sub-set of binding complexes.

FIG. 3 shows the detection methodology for a micro-fluid channel based multiplexed analyzer systems.

FIG. 4 shows the sample preparation method for a microarray based multiplexed analyzer systems.

FIG. 8 shows a schematic of a system for machine learning and analyte quantification.

DETAILED DESCRIPTION

Figure 2:
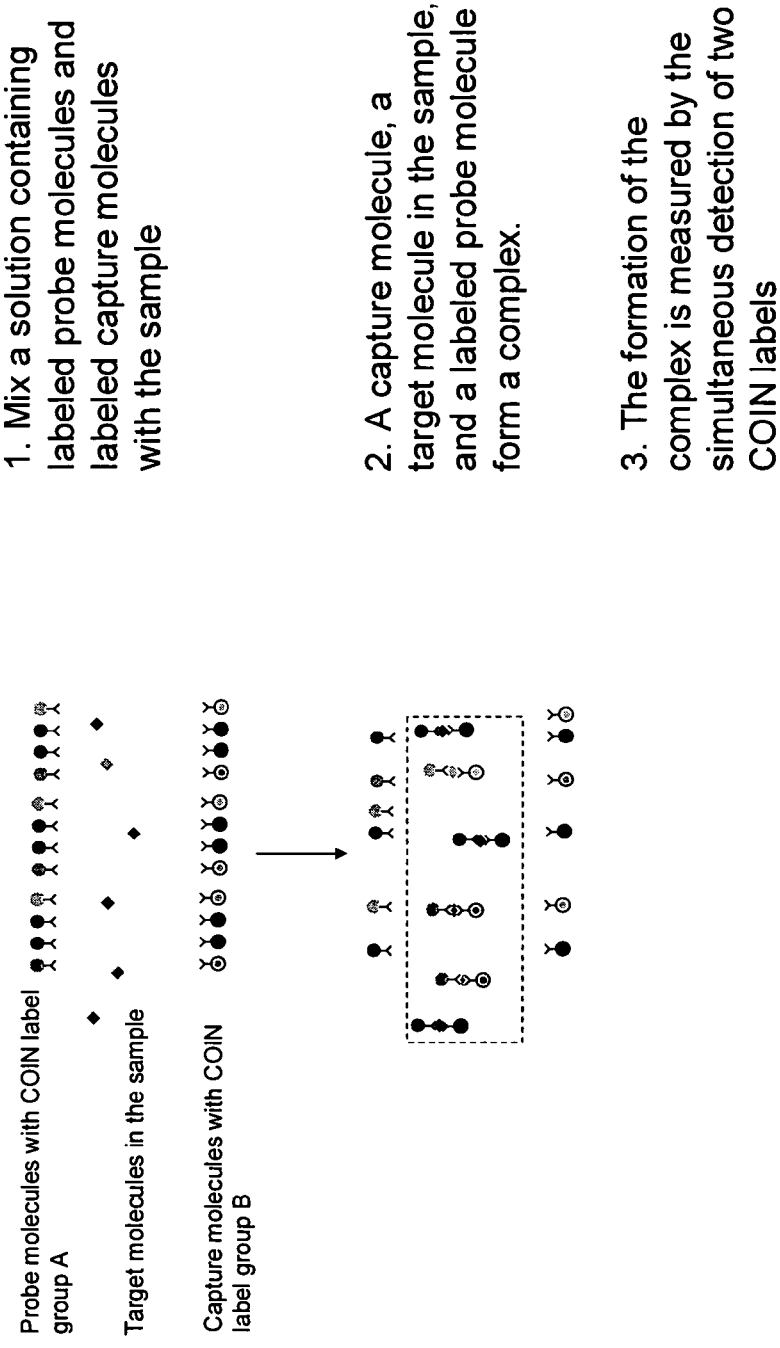
FIG. 2 shows the sample preparation method for a microfluid channel based multiplex analyzer system.

A biological sample often contains many thousands or even more types of biomolecules and clinical diagnosis needs to measure multiple analytes for disease confirmation. Currently, each analyte is measured separately, which requires multiple samples from a patient. The procedure is time consuming and labor intensive. The embodiments of the invention allow for multiple analyte detection from a single sample and a single test, which could be of great interest to clinical diagnosis, and biomedical research as well.

Analytes include nucleic acids (DNA and RNA), which can form double-stranded molecules by hybridization, that is, complementary base pairing. The specificity of nucleic acid hybridization is such that the detection of molecular and/or nanomaterials binding events can be done through electrical readout of polarization changes caused by the interaction of charged target molecules (DNA, RNA, proteins, for example.) and chemically modified nanomaterials (carbon nanotubes, nanowires, nanoparticles functionalized with DNA, for example) with complementary molecular probes (DNA, RNA, anti-body, for example) attached to the electrodes (such as Au, Pt, for example). This specificity of complementary base pairing also allows thousands of hybridization to be carried out simultaneously in the same experiment on a DNA chip (also called a DNA array).

Molecular probes are immobilized on the surface of individually addressable electrode arrays through the surface functionalization techniques. Electrodes allow polarization changes to be electrically detected. The polymer arrays of the embodiment of the invention could be a DNA array (collections of DNA probes on a shared base) comprising a dense grid of spots (often called elements or pads) arranged on a miniature support. Each spot could represent a different gene.

The probe in a DNA chip is usually hybridized with a complex RNA or cDNA target generated by making DNA copies of a complex mixture of RNA molecules derived from a particular cell type (source). The composition of such a target reflects the level of individual RNA molecules in the source. The intensities of the signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example herein below. However, other equivalent conventional procedures can, of course, also be used.

As used in the specification and claims, the singular forms "a", "an" and "the" include plural references unless the context clearly dictates otherwise. For example, the term "an array" may include a plurality of arrays unless the context clearly dictates otherwise.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "probe" or "probe molecule" refers to a molecule attached to the substrate of the array, which is typically cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism.

The term "target" or "target molecule" refers to a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires and nanoparticles. The target molecule may be fluorescently labeled DNA or RNA.

The terms "die," "polymer array chip," "DNA array," "array chip," "DNA array chip," "bio-chip" or "chip" are used interchangeably and refer to a collection of a large number of probes arranged on a shared substrate which could be a portion of a silicon wafer, a nylon strip or a glass slide.

The term "molecule" generally refers to a chemical made up of two or more atoms and includes a macromolecule, biomolecule or polymer as described herein. However, arrays comprising single molecules, as opposed to macromolecules or polymers, are also within the scope of the embodiments of the invention. The term "biomolecule" refers to any organic molecule that is part of a living organism. A "complex of a biomolecule" refers to a structure made up of two or more types of biomolecules. Examples of a complex of biomolecule include a cell or viral particles. A cell can include bacteria, fungi, animal mammalian cell, for example.

"Predefined region," "spot" "binding area" or "pad" refers to a localized area on a solid support which is, was, or is intended to be used for the formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 $cm^2$ or less than 1 $mm^2$, and still more preferably less than 0.5 $mm^2$. In most preferred embodiments the regions have an area less than about 10,000 $\mu m^2$ or, more preferably, less than 100 $\mu m^2$. Additionally, multiple copies of the polymer will typically be synthesized within any preselected region. The number of copies can be in the thousands to the millions. More preferably, a die of a wafer contains at least 400 spots in, for example, an at least 20×20 matrix. Even more preferably, the die contains at least 2048 spots in, for example, an at least 64×32 matrix, and still more preferably, the die contains at least 204,800 spots in, for example, an at least 640×320 array. A spot could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped.

A "microcoil" refers to a localized microelectromagnet on or in a solid support which is, was, or is intended to be used for the formation of a selected molecule under the influence of magnetic field. Integrated microcoils in an array may have any convenient shape, e.g., circular, rectangular, elliptical, wedge-shaped, etc. In some embodiments of the invention, the microcoil could be smaller than about 1 $cm^2$ or less than 1 $mm^2$, and still more preferably less than 0.5 $mm^2$. In most preferred embodiments the microcoil could have an area less than about 10,000 $\mu m^2$ or, more preferably, less than 100 $\mu m^2$. For independent magnetic field control, each microcoil is connected to its own on-chip current source. The operating principle of the microcoil array for cell manipulation is to create and move magnetic field peaks by modulating currents in the microcoils. For instance, by activating only one microcoil in the array, a magnetic bead suspended in fluid will be attracted to the field peak at the center of the microcoil on the surface of the IC having the microcoil. Subsequently, by turning off the microcoil while activating an adjacent one, the magnetic field peak is moved to the center of the adjacent microcoil, transporting the magnetic bead to the new peak location. The spatial resolution of the manipulation is determined by the spacing between two neighboring coils. For precise spatial control of individual magnetic beads, the microcoil could be carefully designed to generate a single magnetic field peak on the chip surface. Note that while the microcoil generally produces a single magnetic peak on the chip surface, multiple magnetic peaks can exist below the surface.

An "electrode" is a body or a location at which an electrochemical reaction occurs. The term "electrochemical" refers to an interaction or interconversion of electric and chemical phenomena. A "functionalized electrode" is an electrode of a microchip array having a probe molecule that has a specific chemical affinity to a target molecule. An "unfunctionalized electrode" is an electrode of a microchip array having no probe molecule or having a probe molecule that has no specific chemical affinity to a target molecule.

The electrodes used in embodiments of the invention may be composed of, but are not limited to, metals such as iridium and/or platinum, and other metals, such as, palladium, gold, silver, copper, mercury, nickel, zinc, titanium, tungsten, aluminum, as well as alloys of various metals, and other conducting materials, such as, carbon, including glassy carbon, reticulated vitreous carbon, basal plane graphite, edge plane graphite and graphite. Doped oxides such as indium-tin oxide and semiconductors such as silicon oxide and gallium arsenide are also contemplated. Additionally, the electrodes may be composed of conducting polymers, metal doped polymers, conducting ceramics and conducting clays. Among the metals, platinum and palladium are especially preferred because of the advantageous properties associated with their ability to absorb hydrogen, i.e., their ability to be "preloaded" with hydrogen before being used in the methods of the invention.

The electrodes may be connected to an electric source in any known manner. Preferred ways of connecting the electrodes to the electric source include CMOS (complementary metal oxide semiconductor) switching circuitry, radio and microwave frequency addressable switches, light addressable switches, direct connection from an electrode to a bond pad on the perimeter of a semiconductor chip, and combinations thereof. CMOS switching circuitry involves the connection of each of the electrodes to a CMOS transistor switch. The switch could be accessed by sending an electronic address signal down a common bus to SRAM (static random access memory) circuitry associated with each electrode. When the switch is "on", the electrode is connected to an electric source. Radio and microwave frequency addressable switches involve the electrodes being switched by a RF or microwave signal. This allows the switches to be thrown both with and/or without using switching logic. The switches can be tuned to receive a particular frequency or modulation frequency and switch without switching logic. Light addressable switches are switched by light. In this method, the electrodes can also be switched with and without switching logic. The light signal can be spatially localized to afford switching without switching logic. This could be accomplished, for example, by scanning a laser beam over the electrode array; the electrode being switched each time the laser illuminates it.

In some aspects, a predefined region can be achieved by physically separating the regions (i.e., beads, resins, gels, etc.) into wells, trays, etc.

A "protecting group" is a moiety which is bound to a molecule and designed to block one reactive site in a molecule, but may be spatially removed upon selective exposure to an activator or a deprotecting reagent. Several examples of protecting groups are known in the literature. The proper selection of protecting group (also known as protective group) for a particular synthesis would be governed by the overall methods employed in the synthesis. Activators include, for example, electromagnetic radiation, ion beams, electric fields, magnetic fields, electron beams, x-ray, and the like. A deprotecting reagent could include, for example, an acid, a base or a free radical. Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with an embodiment of the invention preferably include all acid and base labile protecting groups. For example, peptide amine groups are preferably protected by t-butyloxycarbonyl (BOC) or benzyloxycarbonyl (CBZ), both of which are acid labile, or by 9-fluorenylmethoxycarbonyl (FMOC), which is base labile. Additionally, hydroxyl groups on phosphoramidites may be protected by dimethoxytrityl (DMT), which is acid labile. Exocyclic amine groups on nucleosides, in particular on phosphoramidites, are preferably protected by dimethylformamidine on the adenosine and guanosine bases, and isobutyryl on the cytidine bases, both of which are base labile protecting groups. This protection strategy is known as fast oligonucleotide deprotection (FOD).

Any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

Additional protecting groups that may be used in accordance with an embodiment of the invention include acid labile groups for protecting amino moieties: tertbutyloxycarbonyl, -tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha.,.alpha.-dimethyl-3,5-dimethyloxybenzyloxy-carbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl; and basic labile groups for protecting phosphotriester groups: cyanoethyl.

An "electrochemical reagent" refers to a chemical generated at a selected electrode by applying a sufficient electrical potential to the selected electrode and is capable of electrochemically removing a protecting group from a chemical functional group. The chemical group would generally be attached to a molecule. Removal of a protecting group, or "deprotection," in accordance with the invention, preferably occurs at a particular portion of a molecule when a chemical reagent generated by the electrode acts to deprotect or remove, for example, an acid or base labile protecting group from the molecule. This electrochemical deprotection reaction may be direct, or may involve one or more intermediate chemical reactions that are ultimately driven or controlled by the imposition of sufficient electrical potential at a selected electrode.

Electrochemical reagents that can be generated electrochemically at an electrode fall into two broad classes: oxidants and reductants. Oxidants that can be generated electrochemically, for example, include iodine, iodate, periodic acid, hydrogen peroxide, hypochlorite, metavanadate, bromate, dichromate, cerium (IV), and permanganate ions. Reductants that can be generated electrochemically, for example, include chromium (II), ferrocyanide, thiols, thiosulfate, titanium (III), arsenic (III) and iron (II) ions. The miscellaneous reagents include bromine, chloride, protons and hydroxyl ions. Among the foregoing reagents, protons, hydroxyl, iodine, bromine, chlorine and thiol ions are preferred.

The generation of and electrochemical reagent of a type of chemical species requires that the electric potential of the electrode that generates the electrochemical reagent have a certain value, which may be achieved by specifying either the voltage or the current. There are two ways to achieve the potential at this electrode: either the voltage may be specified at a value or the current can be determined such that it is sufficient to provide a voltage. The range between the minimum and maximum potential values could be determined by the type of electrochemical reagent chosen to be generated.

An "activating group" refers to those groups which, when attached to a particular chemical functional group or reactive site, render that site more reactive toward covalent bond formation with a second chemical functional group or reactive site.

A "polymeric brush" ordinarily refers to polymer films comprising chains of polymers that are attached to the surface of a substrate. The polymeric brush could be a functionalized polymer films which comprise functional groups such as hydroxyl, amino, carboxyl, thiol, amide, cyanate, thiocyanate, isocyanate and isothio cyanate groups, or a combination thereof, on the polymer chains at one or more predefined regions. The polymeric brushes of the embodiment of the invention are capable of attachment or stepwise synthesis of macromolecules thereon.

A "linker" molecule refers to any of those molecules described supra and preferably should be about 4 to about 40 atoms long to provide sufficient exposure. The linker molecules may be, for example, aryl acetylene, ethylene glycol oligomers containing 2-10 monomer units, diamines, diacids, amino acids, among others, and combinations thereof. Alternatively, the linkers may be the same molecule type as that being synthesized (i.e., nascent polymers), such as polynucleotides, oligopeptides, or oligosaccharides.

The linker molecule or substrate itself and monomers used herein are provided with a functional group to which is bound a protective group. Generally, the protective group is on the distal or terminal end of a molecule. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups, there could be an additional step of reactivation. In some embodiments, this will be done by heating.

The polymeric brush or the linker molecule may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis. The cleavable group could be acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

The polymeric brush or the linker molecule could be of sufficient length to permit polymers on a completed substrate to interact freely with binding entities (monomers, for example) exposed to the substrate. The polymeric brush or the linker molecule, when used, could preferably be long enough to provide sufficient exposure of the functional groups to the binding entity. The linker molecules may include, for example, aryl acetylene, ethylene glycol oligomers containing from 2 to 20 monomer units, diamines, diacids, amino acids, and combinations thereof. Other linker molecules may be used in accordance with the different embodiments of the present invention and will be recognized by those skilled in the art in light of this disclosure. In one embodiment, derivatives of the acid labile 4,4'-dimethyoxytrityl molecules with an exocyclic active ester can be used in accordance with an embodiment of the invention. More preferably, N-succinimidyl-4[bis-(4-methoxyphenyl)-chloromethyl]-benzoate is used as a cleavable linker molecule during DNA synthesis.

Alternatively, other manners of cleaving can be used over the entire array at the same time, such as chemical reagents, light or heat.

"Monomer" as used herein refers to those monomers that are used to form a polymer. However, the meaning of the monomer will be clear from the context in which it is used. The monomers in a given polymer or macromolecule can be identical to or different from each other. A monomer can be a small or a large molecule, regardless of molecular weight. Furthermore, each of the monomers may be protected members which are modified after synthesis.

The monomers for forming the polymers of the embodiments of the invention, e.g., a polymeric brush or a linker molecule, have for example the general structure:

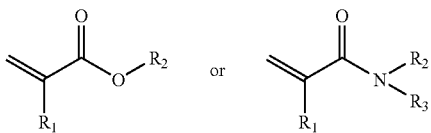

wherein $R_1$ is hydrogen or lower alkyl; $R_2$ and $R_3$ are independently hydrogen, or —Y-Z, wherein Y is lower alkyl, and Z is hydroxyl, amino, or C(O)—R, where R is hydrogen, lower alkoxy or aryloxy.

The term "alkyl" refers to those groups such as methyl, ethyl, propyl, butyl etc, which may be linear, branched or cyclic.

The term "alkoxy" refers to groups such as methoxy, ethoxy, propoxy, butoxy, etc., which may be linear, branched or cyclic.

The term "lower" as used in the context of lower alkyl or lower alkoxy refers to groups having one to six carbons.

The term "aryl" refers to an aromatic hydrocarbon ring to which is attached an alkyl group. The term "aryloxy" refers to an aromatic hydrocarbon ring to which is attached an alkoxy group. One of ordinary skill in the art would readily understand these terms.

Other monomers for preparing macromolecules of the embodiments of the invention are well-known in the art. For example, when the macromolecule is a peptide, the monomers include, but are not restricted to, for example, amino acids such as the L-amino acids, the D-amino acids, and the synthetic and/or natural amino acids. When the macromolecule is a nucleic acid, or polynucleotide, the monomers include any nucleotide. When the macromolecule is a polysaccharide, the monomers can be any pentose, hexose, heptose, or their derivatives.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-500 nanometer range. Preferably, a nanomaterial has properties and functions because of the size and can be manipulated and controlled on the atomic level.

A "carbon nanotube" refers to a fullerene molecule having a cylindrical or toroidal shape. A "fullerene" refers to a form of carbon having a large molecule consisting of an empty cage of sixty or more carbon atoms.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Phosphoramidites protected in this manner are known as FOD phosphoramidites.

Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

An "antibody" is any of various bodies or substances in the blood which act in antagonism to harmful foreign bodies, as toxins or the bacteria producing the toxins. Normal blood serum apparently contains various antibodies, and the introduction of toxins or of foreign cells also results in the development of their specific antibodies. For example, an antibody is a Y-shaped protein on the surface of B cells that is secreted into the blood or lymph in response to an antigenic stimulus, such as a bacterium, virus, parasite, or transplanted organ, and that neutralizes the antigen by binding specifically to it; an immunoglobulin.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

A "carbohydrate" is a compound with carbon, hydrogen and oxygen usually in a proportion to form water with the general formula $C_n(H_2O)_n$. Carbohydrates can also be called chemically as neutral compounds of carbon, hydrogen and oxygen. Carbohydrates are mainly sugars and starches, together constituting one of the three principal types of nutrients used as energy sources (calories) by the body. Carbohydrates come in simple forms such as sugars and in complex forms such as starches and fiber. The body breaks down most sugars and starches into glucose, a simple sugar that the body can use to feed its cells. Complex carbohydrates are derived from plants. Dietary intake of complex carbohydrates can lower blood cholesterol when they are substituted for saturated fat. Carbohydrates are classified into mono, di, tri, poly and heterosaccharides. The smallest carbohydrates are monosaccharides such as glucose whereas polysaccharides such as starch, cellulose and glycogen can be large and even indeterminate in length.

A "lipid" is defined as a substance such as a fat, oil or wax that dissolves in alcohol but not in water. Lipids contain carbon, hydrogen and oxygen but have far less oxygen proportionally than carbohydrates. Lipids are an important part of living cells. Together with carbohydrates and proteins, lipids are the main constituents of plant and animal cells. Cholesterol and triglycerides are lipids. Lipids are easily stored in the body. They serve as a source of fuel and are an important constituent of the structure of cells. Lipids include fatty acids, neutral fats, waxes and steroids (like cortisone). Compound lipids (lipids complexed with another type of chemical compound) comprise the lipoproteins, glycolipids and phospholipids.

An "antigen" a substance that is capable of causing the production of an antibody. For example, when an antigen is introduced into the body, it stimulates the production of an antibody. Antigens include toxins, bacteria, foreign blood cells, and the cells of transplanted organs.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies. Ligands to cells or cell-derived molecules, which can include both known and unknown ligands as well as putative drug candidates that are either unattached to other solid supports or attached to surfaces or particle-like structures, could interact with other cell-derived molecules in a manner such that binding between two binding partners occurs and can be detected. One of the binding partners or its attached support can additionally be derivatized with a substance that can be recognized and quantified by a detection apparatus. This complex (through interaction) is then brought into the presence of the detection apparatus using characteristics of the associated complex that differentiate it from the unassociated binding partners.

An "affinity binding partner" or "binding partner" could be a probe or a ligand defined above.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. However, as the term receptor is used herein, no difference in meaning is intended. A "ligand receptor pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

By "analyte" is meant any molecule or compound. An analyte can be in the solid, liquid, gaseous or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, peptide nucleic acids (PNA), restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

The analyte can further be a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus. Also, the analyte could be charged. A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Bioanalyte can also be complex of molecules or compounds in organized or random fashion, such cells, virus, bacteria, fungi, etc.

"Specific binding" is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide hybridization interactions, and so forth.

"Non-specific binding" is non-covalent binding between molecules that is relatively independent of specific surface structures. Non-specific binding may result from several factors including hydrophobic interactions between molecules.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes can have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The monoepitopic ligand analytes can generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The term "reporter" means a detectable moiety. The reporter can be detected, for example, by Raman spectroscopy. Generally, the reporter and any molecule linked to the reporter can be detected without a second binding reaction. The reporter can be COIN (composite-organic-inorganic nanoparticle), magnetic-COIN, quantum dots, and other Raman or fluorescent tags, for example.

The term "COIN" refers to a composite-organic-inorganic nanoparticle(s). The COIN could be surface-enhanced Raman spectroscopy (SERS)-active nanoparticles incorporated into a gel matrix and used in certain other analyte separation techniques described herein. COINs are composite organic-inorganic nanoparticles. These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanoparticle. The COINs can further comprise an organic layer overlying the metal layer, which organic layer comprises the probe. Suitable probes for attachment to the surface of the SERS-active nanoparticles include, without limitation, antibodies, antigens, polynucleotides, oligonucleotides, receptors, ligands, and the like.

The metal required for achieving a suitable SERS signal is inherent in the COIN, and a wide variety of Raman-active organic compounds can be incorporated into the particle. Indeed, a large number of unique Raman signatures can be created by employing nanoparticles containing Raman-active organic compounds of different structures, mixtures, and ratios. Thus, the methods described herein employing COINs are useful for the simultaneous detection of many analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoparticles described herein as COINs. This situation results in increased sensitivity compared to Raman-techniques that do not utilize COINs.

COINs could be prepared using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs could be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. This COIN can typically be isolated by membrane filtration. In addition, COINs of different sizes can be enriched by centrifugation.

The COINs can include a second metal different from the first metal, wherein the second metal forms a layer overlying the surface of the nanoparticle. To prepare SERS-active nanoparticle, COINs are placed in an aqueous solution containing suitable second metal cations and a reducing agent. The components of the solution are then subject to conditions that reduce the second metallic cations so as to form a metallic layer overlying the surface of the nanoparticle. In certain embodiments, the second metal layer includes metals, such as, for example, silver, gold, platinum, aluminum, and the like. These COINs can be isolated and/or enriched in the same manner as explained below. Typically, COINs are substantially spherical and range in size from about 20 nm to 60 nm. The size of the nanoparticle is selected to be about one-half the wavelength of light used to irradiate the COINs during detection.

Typically, organic compounds of COINs are attached to a layer of a second metal by covalently attaching organic compounds to the surface of the metal layer Covalent attachment of an organic layer to the metallic layer can be achieved in a variety ways well known to those skilled in the art, such as for example, through thiol-metal bonds. In alternative embodiments, the organic molecules attached to the metal layer can be crosslinked to form a molecular network.

The COIN(s) can include cores containing magnetic materials, such as, for example, iron oxides, and the like such that the COIN is a magnetic COIN. Magnetic COINs can be handled without centrifugation using commonly available magnetic particle handling systems. Indeed, magnetism can be used as a mechanism for separating biological targets attached to magnetic COIN particles tagged with particular biological probes.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

When "fluorescent compounds" are incorporated into COINs, the fluorescent compounds can include, but are not limited to, dyes, intrinsically fluorescent proteins, lanthanide phosphors, and the like. Dyes useful for incorporation into COINs include, for example, rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

Multiplex testing of a complex sample would generally be based on a coding system that possesses identifiers for a large number of reactants in the sample. The primary variable that determines the achievable numbers of identifiers in currently known coding systems is, however, the physical dimension. Tagging techniques, based on surface-enhanced Raman scattering (SERS) of fluorescent dyes, could be used in the embodiments of this invention for developing chemical structure-based coding systems. The organic compound-assisted metal fusion (OCAM) method could be used to produce composite organic-inorganic nanoparticles (COIN) that are highly effective in generating SERS signals allows synthesis of COIN labels from a wide range of organic compounds to produce sufficient distinguishable COIN Raman signatures to assay any complex biological sample. Thus COIN particles may be used as a coding system for multiplex and amplification-free detection of bioanalytes at near single molecule levels.

COIN particles generate intrinsic SERS signal without additional reagents. Using the OCAMF-based COIN synthesis chemistry, it is possible to generate a large number of different COIN signatures by mixing a limited number of Raman labels for use in multiplex assays in different ratios and combinations. In a simplified scenario, the Raman spectrum of a sample labeled with COIN particles may be characterized by three parameters: (a) peak position (designated as L), which depends on the chemical structure of Raman labels used and the umber of available labels, (b) peak number (designated as M), which depends on the number oflabels used together in a single COIN, and (c) peak height (designated as i), which depends on the ranges of relative peak intensity.

The total number of possible distinguishable Raman signatures (designated as T) may be calculated from the following equation:

$$T = \sum_{k=1}^{M} \frac{L!}{(L-k)!k!} P(i,k)$$

where $P(i, k) = i^k - i + 1$, being the intensity multiplier which represents the number of distinct Raman spectra that may be generated by combining k (k=1 to M) labels for a given i value. The multiple organic compounds may be mixed in various combinations, numbers and ratios to make the multiple distinguishable Raman signatures. It has been shown that spectral signatures having closely positioned peaks (15 cm$^{-1}$) may be resolved visually. Theoretically, over a million of Raman signatures may be made within the Raman shift range of 500-2000 cm$^{-1}$ by incorporating multiple organic molecules into COIN as Raman labels using the OCAMF-based COIN synthesis chemistry.

Thus, OCAMF chemistry allows incorporation of a wide range of Raman labels into metal colloids to perform parallel synthesis of a large number of COIN labels with distinguishable Raman signatures in a matter of hours by mixing several organic Raman-active compounds of different structures, mixtures, and ratios for use in the invention methods described herein.

COINs may be used to detect the presence of a particular target analyte, for example, a nucleic acid, oligonucleotide, protein, enzyme, antibody or antigen. The nanoparticles may also be used to screen bioactive agents, i.e. drug candidates, for binding to a particular target or to detect agents like pollutants. Any analyte for which a probe moiety, such as a peptide, protein, oligonucleotide or aptamer, may be designed can be used in combination with the disclosed nanoparticles.

Also, SERS-active COINs that have an antibody as binding partner could be used to detect interaction of the Raman-active antibody labeled constructs with antigens either in solution or on a solid support. It will be understood that such immunoassays can be performed using known methods such as are used, for example, in ELISA assays, Western blotting, or protein arrays, utilizing a SERS-active COIN having an antibody as the probe and acting as either a primary or a secondary antibody, in place of a primary or secondary antibody labeled with an enzyme or a radioactive compound. In another example, a SERS-active COIN is attached to an enzyme probe for use in detecting interaction of the enzyme with a substrate.

Another group of exemplary methods could use the SERS-active COINs to detect a target nucleic acid. Such a method is useful, for example, for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art. The oligonucleotide is then used to functionalize a SERS-active COIN. Detection of the specific Raman label in the SERS-active COIN identifies the nucleotide sequence of the oligonucleotide probe, which in turn provides information regarding the nucleotide sequence of the target polynucleotide.

A "quantum dot" is a particle of matter so small that the addition or removal of an electron changes its properties in some useful way. All atoms are, of course, quantum dots, but multi-molecular combinations can have this characteristic. In biochemistry, quantum dots are called redox groups. In nanotechnology, they are called quantum bits or qubits. Quantum dots typically have dimensions measured in nanometers, where one nanometer is $10^{-9}$ meter or a millionth of a millimeter. The fields of biology, chemistry, computer science, and electronics are all of interest to researchers in nanotechnology. An example of the overlapping of these disciplines is a hypothetical biochip, which might contain a sophisticated computer and be grown in a manner similar to the way a tree evolves from a seed. In this scenario, the terms redox group and qubit are equally applicable; it is hard to classify such a chip as either animate or inanimate. The quantum dots in a biochip would each account for at least one data bit, and possibly several.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "oxidation" means losing electron to oxidize. The term "reduction" means gaining electrons to reduce. The term "redox reaction" refers to any chemical reaction which involves oxidation and reduction.

The term "wafer" means a semiconductor substrate. A wafer could be fashioned into various sizes and shapes. It could be used as a substrate for a microchip. The substrate could be overlaid or embedded with circuitry, for example, a pad, via, an interconnect or a scribe line. The circuitry of the wafer could also serve several purpose, for example, as microprocessors, memory storage, and/or communication capabilities. The circuitry can be controlled by the microprocessor on the wafer itself or controlled by a device external to the wafer.

A "scribe line" is typically an "inactive" area between the active dies that provide area for separating the die (usually with a saw). Often, metrology and alignment features populate this area.

A "via" refers to a hole etched in the interlayer of a dielectric which is then filled with an electrically conductive material, preferably tungsten, to provide vertical electrical connection between stacked up interconnect metal lines that are capable of conducting electricity.

"Metal lines" within a die are interconnect lines. Metal interconnect lines do not typically cross the scribe line boundary to electrically connect two dies or, as in the some embodiments of this invention, a multitude of die to one or more wafer pads.

The term "field effect transistor" (FET) is a family of transistors that rely on an electric field to control the conductivity of a "channel" in a semiconductor material. FETs, like all transistors, can be thought of as voltage-controlled resistors. Most FETs are made using conventional bulk semiconductor processing techniques, using the single-crystal semiconductor wafer as the active region, or channel.

The term "CMOS" means complementary metal oxide semiconductor.

"Micro-Electro-Mechanical Systems (MEMS)" include the integration of mechanical elements, sensors, actuators, and electronics on a common silicon substrate through microfabrication technology. MEMS often combine electrical and mechanical functionalities on a single substrate. An example of a MEMS device could be a small mechanical chamber where two liquids (biofluids, drugs, chemicals etc.) are mixed and a sensor interprets the results. MEMS could also be integrated with logic functionalities i.e. having a CMOS circuit to perform some algorithm with the data provided by the sensor. The CMOS circuit could then have circuit elements that transport the results of the algorithm and the sensor input to another device (i.e. output to further devices comprising the overall micro-system). While the electronics are fabricated using integrated circuit (IC) process sequences (e.g., CMOS, Bipolar, or BICMOS processes), the micromechanical components could be fabricated using compatible "micro-machining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are generally manufactured using batch fabrication techniques similar to those used for integrated circuits, unprecedented levels of functionality, reliability, and sophistication can be placed on a small silicon chip at a relatively low cost.

One of the mechanical processes typically performed by MEMS is transporting small amounts of fluids through channels, which are called "microfluidic channels." These channels are frequently embedded in a covering layer (hereafter called: embedding layer). One example of a microfluidic channel used in MEMS is in an electrokinetic pump. Electrokinetic pumps use an ionic fluid and a current imposed at one end of the channel and collected at the other end of the channel. This current in the ionic fluid impels the ionic fluid towards the collection pad of the electrokinetic pump.

The term "waveguide" refers to a device that controls the propagation of an electromagnetic wave so that the wave is forced to follow a path defined by the physical structure of the guide. Generally speaking, the electric and magnetic fields of an electromagnetic wave have a number of possible arrangements when the wave is traveling through a waveguide. Each of these arrangements is known as a mode of propagation. Optical waveguides are used at optical frequencies. An "optical waveguide" is any structure having the ability to guide optical energy. Optical waveguides may be (a) thin-film deposits used in integrated optical circuits (IOCs) or (b) optical fibers.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

One embodiment of the invention relates to a complex comprising a first binding partner, a first reporter associated with the first binding partner, an analyte, a second binding partner, and a second reporter associated with the second binding partner. Preferably, the complex comprises the first reporter, the first binding partner, the analyte, the second binding partner, and the second reporter in this order. Preferably, the first reporter or the second reporter comprises a nanomaterial having more than 50%, 60%, 70%, 80% or 90% by weight of inorganic content. The analyte and the binding partners preferably comprise a biomolecule such as antibody, a protein, a carbohydrate, a lipid, an antigen, a receptor, or a ligand, or a macromolecule. The receptor preferably comprises a quantum dot, a Raman tag, a fluorescent tag, a composite-organic-inorganic nanoparticle (COIN) or a magnetic COIN. The magnetic COIN could comprise a metal particle with at least one Raman active organic compound adsorbed on the metal particle. In one variation, the first reporter and the second reporter are associated to the first binding partner and the second binding partner, respectively, through a molecule in between the first or second reporter and the first or second binding partner.

Another embodiment of the invention relates to a device for analysis comprising a microfluidic channel (MFC) comprising a plurality of first binding partners immobilized on spots in the MFC, wherein the MFC comprises an inorganic support and an optically transparent cover and further comprises a plurality of probes (i.e., binding partners) optionally with COINs or magnetic COINs immobilized on spots in the MFC. The binding partner immobilized on the spot could be attached to an analyte, which in turn could be attached another binding partner attached to the analyte and a reporter such as a COIN or a magnetic-COIN.

The device for fluidic separation can be made by using soft lithography method with poly-dimethyl siloxane. With these techniques it is possible to generate patterns with critical dimensions as small as 30 nm. These techniques use transparent, elastomeric polydimethylsiloxane (PDMS) "stamps" with patterned relief on the surface to generate features. The stamps can be prepared by casting prepolymers against masters patterned by conventional lithographic techniques, as well as against other masters of interest. Several different techniques are known collectively as soft lithography. They are as described below:

Near-Field Phase Shift Lithography. A transparent PDMS phase mask with relief on its surface is placed in conformal contact with a layer of photoresist. Light passing through the stamp is modulated in the near-field. If the relief on the surface of the stamp shifts the phase of light by an odd multiple of (, a node in the intensity is produced. Features with dimensions between 40 and 100 nm are produced in photoresist at each phase edge.

Replica Molding. A PDMS stamp is cast against a conventionally patterned master. Polyurethane is then molded against the secondary PDMS master. In this way, multiple copies can be made without damaging the original master. The technique can replicate features as small as 30 nm.

Micromolding in Capillaries (MIMIC). Continuous channels are formed when a PDMS stamp is brought into conformal contact with a solid substrate. Capillary action fills the channels with a polymer precursor. The polymer is cured and the stamp is removed. MIMIC is able to generate features down to 1 µm in size.

Microtransfer Molding ((TM). A PDMS stamp is filled with a prepolymer or ceramic precursor and placed on a substrate. The material is cured and the stamp is removed. The technique generates features as small as 250 nm and is able to generate multilayer systems.

Solvent-assisted Microcontact Molding (SAMIM). A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontact Printing ((CP). An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used in other groups include micromachining of silicon for microelectricalmechanical systems (MEMS), and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm.

Applications of soft lithography in the near future could include simple optical devices, such as polarizers, filters, wire grids, and surface acoustic wave (SAW) devices. Longer term goals include working toward optical data storage systems, flat panel displays, and quantum devices. Soft lithographic techniques are currently not competitive with conventional photolithography for multilayer fabrication where there are critical requirements for pattern regularity.

Standard lithography on silicone wafer or silica glass could also be used to fabricate the devices of the embodiments of this invention. Chambers or channels can be make from the devices, fluidic flow can be controlled by pressure gradient, electrical field gradient, gravity, heat gradient etc. The binding complexes can also be separated by planar device with a single a plurality of chambers, where the surfaces are modified with polymers (polyethylene glycol (PEG)-dramatized compounds) that can minimize non-specific binding. The substrate (solid support) can be inorganic material (e.g., glass, ceramic) or metal (e.g., aluminum), biomolecules, protein, antibody, nucleic acid can be coated on the surface for specific analyte binding.

The above embodiments could be practiced by the following methods.

Two-reporter method as shown in FIG. 1A: The complexes are formed when an analyte is bound to two affinity binding partners each of which is associated with a reporter. The reporter can be COIN (composite-organic-inorganic nanoparticles), quantum dots and other Raman or fluorescent tags, but COINs will be particularly useful for this purpose. Since many different types of COINs can be made and can be used to conjugate specific antibodies, a large collection of binding complexes can be formed (reporter1-binding partner 1-analyte-binding partner 2-reporter 2). Preferably, reporter 1 is different from reporter 2, which would allow the binding complex formed to be distinguished over a molecule where reporter 1 or reporter 2 is not bound to the analyte. Unbound reporter-binding partners can be separated by size or magnetic property if one of the reporters is paramagnetic. Binding partners can be antibodies, antigens, receptors or ligands. Sub-set of binding complexes is formed by controlling the concentration of the complexes in solution. When multiple binding complexes move through a microfluidic channel, their optical features can be recorded and subsequently analyzed. Positive detection of an analyte is indicated by the detection of two reporters simultaneously as predicted by binding partner specificity.

Spatial position and reporter method as shown in FIG. 1B: A device surface (array) containing multiple binding areas, each of the areas contains a mixture of binding partners (antibodies). The binding areas can be grouped into different compartments or spots, wherein one or more of the compartments or spots could have an organic polymer layer containing a polymeric brush or a linker molecule. Each of the binding area is optionally surrounded by non-binding surface and contains multiple binding partners (different antibodies are mixed and immobilized). The binding surfaces are fabricated to minimize non-specific binding of analytes or reporters or binding partners. A biological sample can be applied individually to a binding surface (area) or sub-set of the binding surfaces of the array. Thus multiple reporters can be located in a single binding area when sandwich binding complexes are formed.

Another embodiment of the invention relates to a device for data collection comprising a beam emitter, a MFC, a spectrometer, particularly a Raman spectrometer, and a detector. The beam emitter is to emit a beam comprising laser. The device could further comprise an optical waveguide between the beam emitter and the MFC. As shown in FIG. 1A, for example, the MFC could comprise a detection site to illuminate a sample comprising a reporter attached to an analyte by the beam. Preferably, the spectrometer is a waveguide based spectrometer to create a phase shift in a Raman signal emitted by the sample. The detector is to detect a characteristic of the Raman signal emitted by the sample. The device could further comprise a microprocessor comprising software or a hardware to identify the Raman signal. The MFC could further comprise a plurality of first binding partners immobilized on spots in the MFC. The MFC could further comprise a plurality of COINs or magnetic COINs immobilized on spots. The MFC could further comprise a microcoil or a Micro-Electro-Mechanical System (MEMS) device.

The devices of FIG. 3 and 5 could be fabricated in the following way in one of the embodiments of the devices. The Fourier transform spectrometer can be fabricated using common semi-conductor fabrication techniques. As an example a silicon wafer could be used as the starting material. An oxide layer could be grown to be used as the bottom cladding of the waveguide. SiON could then be deposited to be used as the waveguide core. This could then have waveguides patterned onto it using wet or dry chemical etching. Control of the index of the MZI arms could be done using the thermo-optic effect by preferentially heating the MZI arms with heaters deposited onto the waveguide. Filters could be integrated onto the waveguide by etching the upper surface or sidewall of the waveguide, or by varying the refractive-index of the waveguide as a function of position. An integrated photodetector could be formed by fabricated a silicon PIN diode on the same substrate as the spectrometer in a way similar to obtaining planar optical devices that is known to persons of ordinary skill in this art.

The method steps and device for the above embodiment of the invention are shown in FIGS. 2 and 3. Even though FIGS. 2 and 3 state "Raman-on-chip," the embodiments of FIGS. 2 and 3 are equally applicable to other analyzers. In particular, the steps are as follows:

1. Mix a solution containing labeled probe molecules and labeled capture molecules with the sample to be analyzed. Both the probe and capture molecules have a COIN label. The sample could be a polymer, a nanomaterial, a carbon nanotube, a nucleotide, or a biomaterial such a peptide, a protein, a ligand, a receptor, a sequence, DNA, RNA, etc.

2. Form a complex, which might involve hybridization, of the COIN labeled capture molecule, a target molecule of the sample and the COIN labeled probe molecule.

3. Detect the complex by simultaneous detection of two COIN labels attached to the complex, which contains the first and second COIN labels of the probe molecule and the target molecule, respectively.

The detection methodology is shown schematically in FIG. 3. The laser light is focused into an optical waveguide, and is delivered to the sample which flows through a micro-fluid channel. The sample scatters light and emits radiation, including Raman emission. The radiation from the sample would be collected by an optical waveguide based spectrometer.

Another embodiment of the invention relates to a device for data collection comprising a beam emitter, a chamber to hold a microarray, a spectrometer and a detector. The beam emitter is to emit a beam comprising laser. The device could further comprise an optical waveguide between the beam emitter and the chamber. The chamber could comprise an optical switch to detect the beam transmitted through the microarray. The spectrometer is preferably a waveguide based spectrometer to create a phase shift in a Raman signal emitted by the sample. The detector is to detect a characteristic of the Raman signal emitted by the sample. The device could further comprise a microprocessor comprising software or a hardware to identify the Raman signal. The device could further comprise a microarray, wherein the microarray comprises a plurality of first binding partners immobilized on spots on the microarray. The microarray could further comprise a plurality of COINs or magnetic COINs immobilized on spots.

Figure 5:
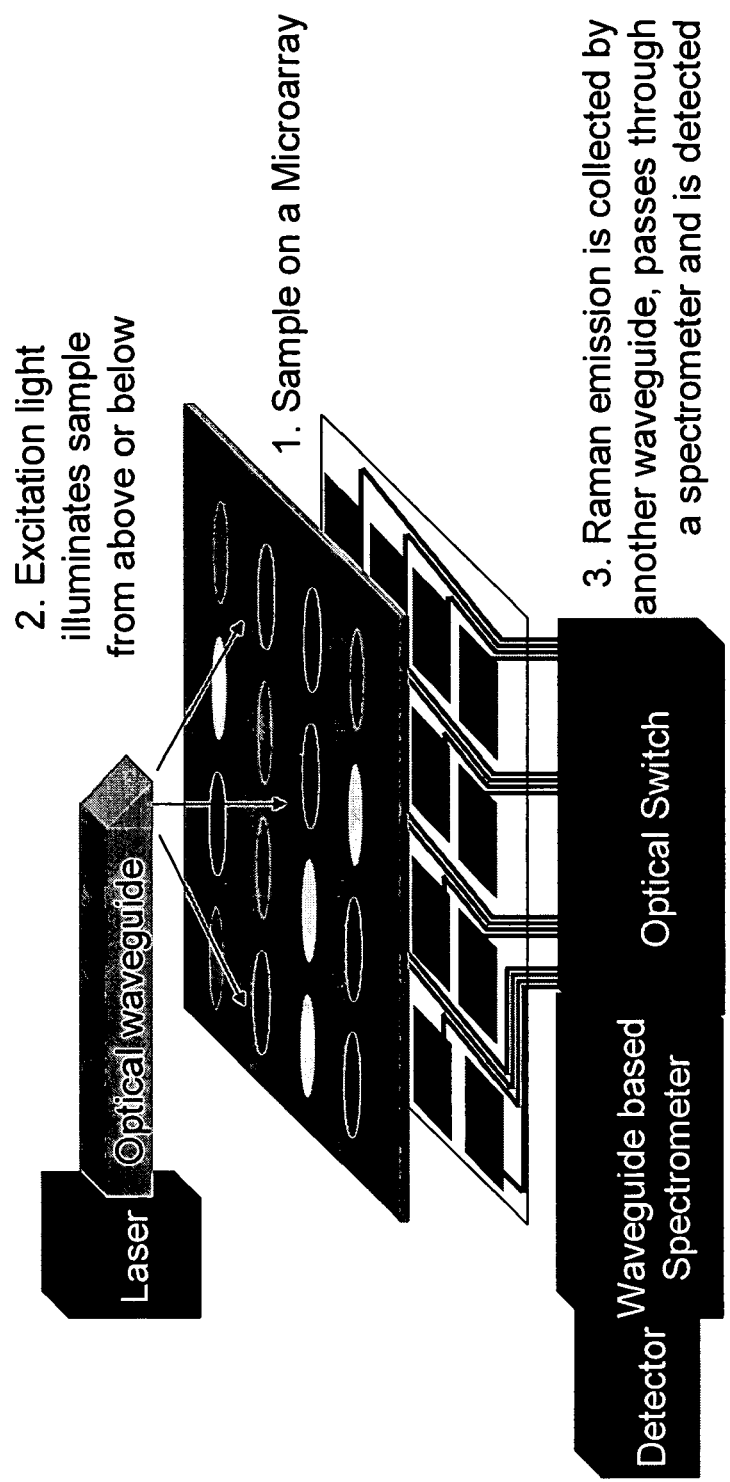
FIG. 5 shows the detection methodology for a micro-array based multiplexed analyzer systems.

The method steps and device of this embodiment of the invention are shown in FIGS. 4 and 5. Even though FIGS. 4 and 5 state "Raman-on-chip," the embodiments of FIGS. 4 and 5 are equally applicable to other analyzers. In particular, the steps are as follows:

1. Introduce the sample and the COIN labeled probe molecules on a substrate of a microarray having spots containing capture molecules (which may or may not be labeled). The sample could be a polymer, a nanomaterial, a carbon nanotube, a nucleotide, or a biomaterial such a peptide, a protein, a ligand, a receptor, a sequence, DNA, RNA, etc.

2. Form a complex, which might involve hybridization, of the capture molecule, a target molecule of the sample and the COIN labeled probe molecule.

3. Detect the complex by detection of one COIN label (or simultaneous detection of two COIN labels if the capture molecule is a COIN labeled capture molecule) attached to the complex.

The detection methodology to detect the sample on the microarray is shown schematically in FIG. 5. The laser light through an optical waveguide is focused on the microarray and the complex on microarray could be illuminated from either above or below the microarray. The complex emits its own signature spectrum comprising a Raman signal. The signature spectrum is collected by an optical waveguide based spectrometer.

In the embodiments of the invention such as the two embodiments described above with reference to FIGS. 2-5, the sample receives the laser light, and emits a unique spectrum of light specific to the COIN. A miniaturized spectrometer and detector could be placed to analyze the spectrum of the emitted light by a miniaturized spectrometer and detector system, for example.

The above embodiments relating to FIGS. 1-5 could further include a sample collection device for collecting the sample that has to be analyzed by the analyzer of the embodiments of the invention. The sample collection device could include suction and sample concentration devices. For example, a solid, liquid or gaseous sample could be sucked into a sample collection device that produces a known background signal. Then, the sample could be concentrated within the sample collection device. For example, a gas could be cooled to create condensate in the sample collection device. By concentrating the sample in the sample collection device, it could reduce the analysis time, particularly for a gaseous sample.

Another embodiment of the invention relates to a device for analyte concentration comprising a first chamber comprising an analyte, a magnetic COIN, and a non-analyte, and a second chamber to hold a concentrate comprising the analyte bound to the magnetic COIN. Preferably, the first chamber is exposed to a first magnetic field and the second chamber is exposed to a second magnetic field, wherein the second magnetic field is different than the first magnetic field. The first chamber could further comprise a magnet to produce the first magnetic field and the second chamber could further comprise a magnet to produce the second magnetic field. In one variation of the device, the first chamber could comprise an instrument to drain a liquid comprising the non-analyte and the second magnetic field is the magnetic field of the earth.

Figure 6:
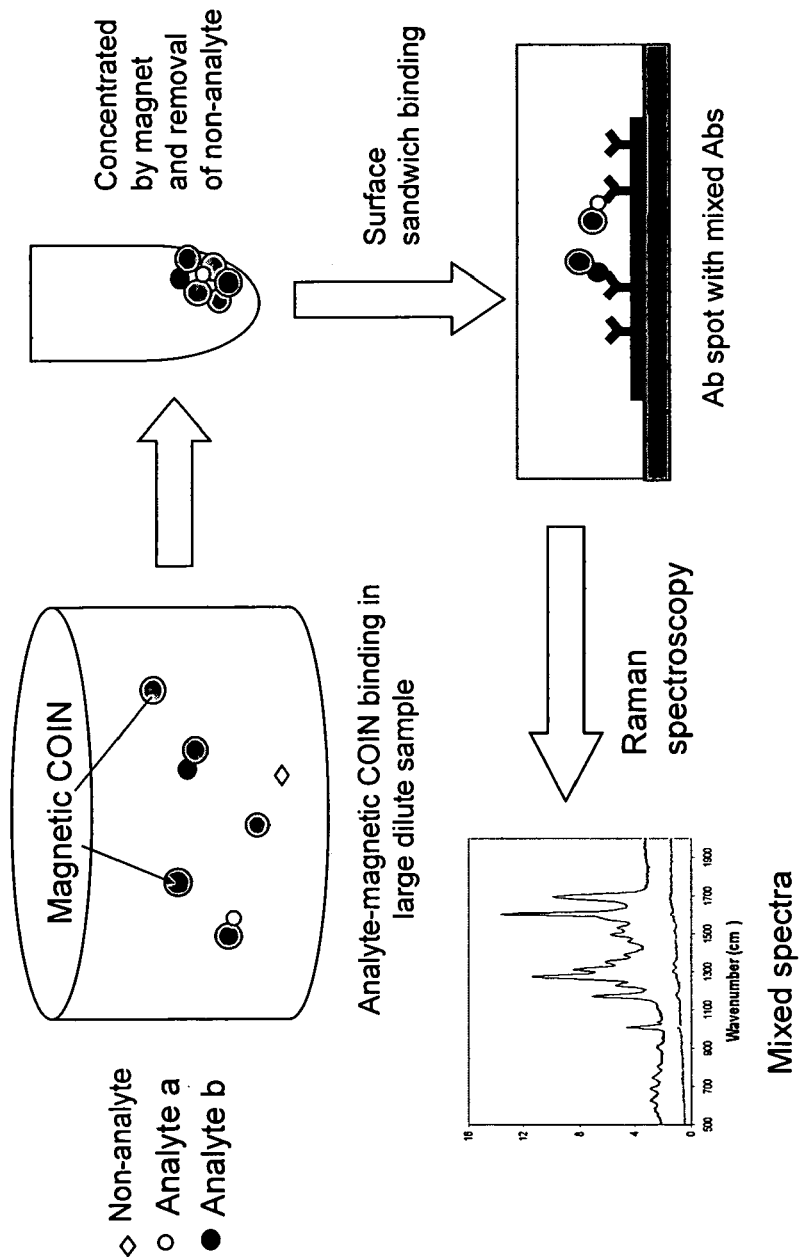
FIG. 6 shows a schematic of the magnetic COIN as reporter and analyte carrier.

In FIG. 6, the sample and the binding partner-conjugated magnetic COINs are mixed in a reaction chambers (centrifugation tubes), after the binding, the binding complexes are cleaned by repeating washing with buffers (applying magnetic field to concentrate and releasing the field to re-suspend the binding complexes). The cleaned binding complexes are then transferred to a binding partner array chip (antibody chip, DNA chip, microfluidic chip etc., for example, see devices of FIG. 1).

The above embodiment could be practiced by the following method and device of FIG. 6:

Magnetic COIN as reporter and analyte carrier as shown in FIG. 6: The device of FIG. 6 allows concentration in magnetic field of certain analytes that are attached to magnetic COINs while excluding non-analytes and other analytes that are not attached to the magnetic COINs. Magnetic COINs can be used as reporters as well as analyte detector and carriers. Analytes in solution can be captured by magnetic COINs that are conjugated with an affinity probe, and concentrated in magnetic field. The concentrated sample with most non-analyte material removed can be placed on an affinity binding surface (with mixed affinity binding partners (Abs)), thus different types sandwich binding complexes can be formed with magnetic COINs as the reporters. The COIN signals can be detected by a Raman spectroscope. Each of the Raman spectra can cover multiple COINs; multiple spectra are needed to collect sufficient data for analysis.

Yet another embodiment of the invention relates to an analyte separation method comprising capturing a first analyte in a solution by a magnetic COIN attached to a first binding partner to form a magnetic COIN-containing complex comprising the first analyte and the magnetic COIN attached to the first binding partner, capturing a second analyte in the solution by a non-magnetic COIN attached to a second binding partner to form a non-magnetic COIN-containing complex comprising the second analyte and the non-magnetic COIN attached to the second binding partner, and grouping the magnetic COIN-containing complex separate from the non-magnetic COIN-containing complex on a surface of a microcoil by generating a local magnetic field on the surface of the microcoil. The method could further comprise controlling the current passing though the microcoil to control a strength of the local magnetic field on the surface of the microcoil. The method could further comprise releasing the magnetic COIN-containing complex from the surface of the microcoil.

The method of manufacturing a microcoil of an embodiment of the device shown in FIG. 7 could be as follows. Briefly, dielectric material, which could be silicon oxide, silicon nitride, or a polymer material, such as benzocyclobutene (BCB) dielectric layer, could be spun on a silicon wafer and cured. This BCB layer defines the separation distance between the coils and the substrate. By using a sputter/lift-off process, the first Cu layer of 3 µm could be deposited and patterned. A second BCB layer of 5 µm could be spun as an inter-layer-dielectric, which also plannerized the surface. Via holes could be opened and a second Cu layer of 3 µm deposited and patterned similarly. The coils could be passivated by using a BCB layer on the top, which could be patterned to expose the probing pads. The width of the Cu trace could range from 12 to 30 µm, the spacing was 12 µm.

The above embodiment could be practiced by the following method.

Figure 7:
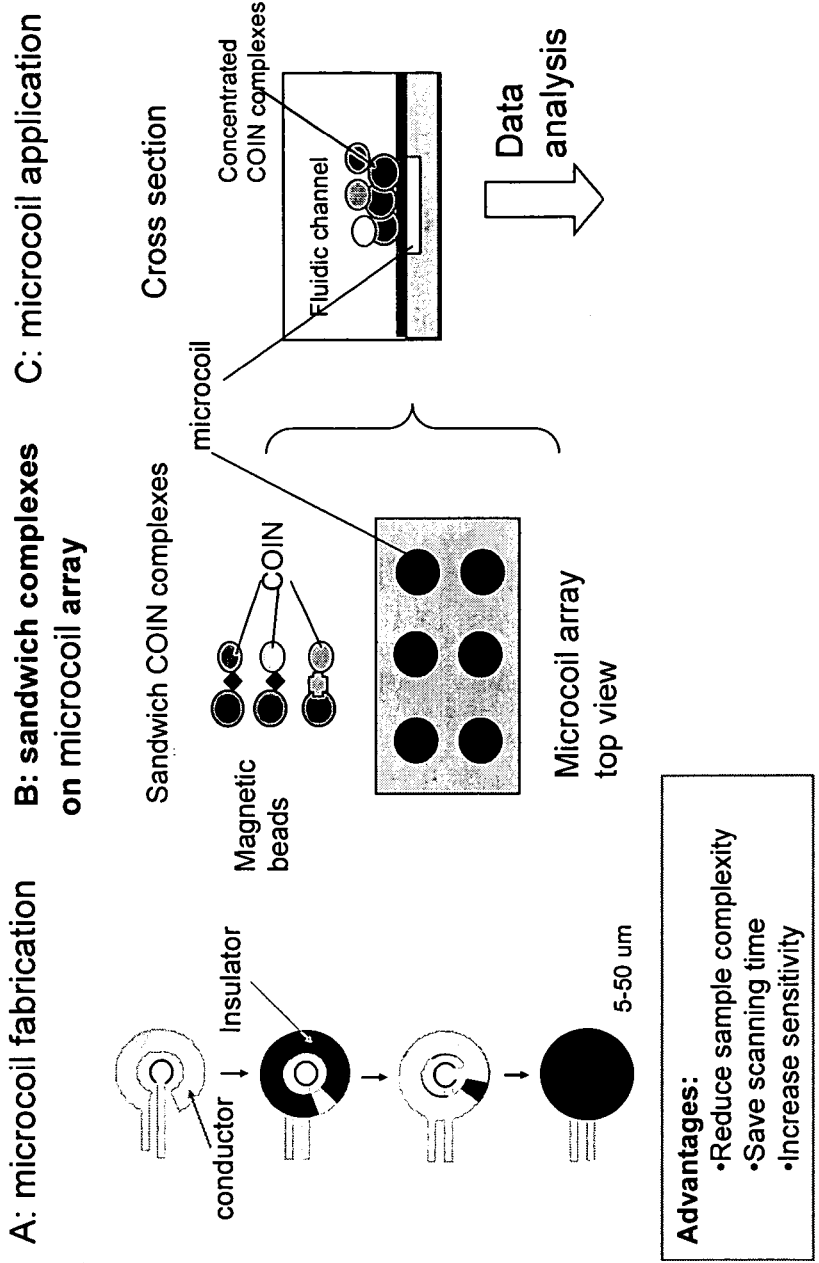
FIG. 7 shows a schematic of the microcoil for concentrating magnetic-COIN sandwich complexes.

Microcoil for concentrating magnetic-COIN sandwich complexes shown in FIG. 7: Similar to FIG. 6, magnetic beads conjugated with a $1^{st}$ set of affinity binding partners (Abs) can be used to capture analytes in solution; non-magnetic COINs conjugated with a $2^{nd}$ set of affinity binding partners are also in contact with the sample. Sandwich binding complexes are formed, which can be sub-grouped on to microcoil surfaces when electricity is applied to generate local magnetic fields. The microcoil magnetic device can be fabricated using lithography techniques. An electronic control board is used to control the current passing the microcoils and thus control the magnetic fields. The binding complexes can be released and new sample can be introduced.

Yet another embodiment of the invention relates to a computer implemented system comprising a first algorithm to simulate spectral features produced by a hypothetical composition comprising a plurality of reporters mixed in different ratios, a second algorithm to compare the simulated spectral features with experimentally obtained spectral features produced by an actual composition comprising a plurality of reporters in different ratios, and a third algorithm to determine a goodness-of-fit between the simulated spectral features and the experimentally obtained spectral features and to iteratively adjust the simulated spectral features by adjusting the hypothetical composition to maximize the goodness-of-fit to meet a pre-set statistical criteria. It is possible that the first, second and third algorithms are bundled into one or more software programs or one or more hardware components. Preferably, the plurality of reporters in the actual composition is associated with a plurality of analytes of a biological sample. In one variation, the goodness-of-fit is maximized by minimizing the difference between the between the simulated spectral features and the experimentally obtained spectral features. Preferably, the difference between the between the simulated spectral features and the experimentally obtained spectral features is determined by a genetic algorithm that qualitatively optimizes the genetic algorithm, by a neural network that optimizes a set of selected parameters for a selected neural patterns or circuits, or by a principal component analysis that statistically decomposes components with maximum likelihood.

For the device of FIG. 8, any device with low Raman background can be used, for example, solution on an aluminum surface, enclosed glass chambers, or any device described above for Raman measurement.

The above embodiment could be practiced by the following method and device of FIG. 8:

Machine learning and analyte quantification: FIG. 8 shows a general scheme of machine learning (software training). Machine learning is a part of multiplex data analysis. When multiple reporters (COINs or quantum dots) are to be used in an assay, spectra of each of these reporters at various concentrations are recorded. In a simplified data analysis a spectral peak (with a unique wavelength or wavenumber) and associated combined parameters such as ratios or polynomials can be used to quickly identify a single reporter. Computer simulation can be used to predict the complex spectral features when a given set of reporters are mixed in a different ratios. The predications will be statistically verified by comparing the computations with actual experiments using pre-determined/known compositions of reporters. The software algorithm and associated parameters are iteratively adjusted to maximize the goodness-of-fit until the resulting converged algorithm and the associated parameters meet pre-set statistical criteria. For example, a variety of algorithms and associated parameters can be used by statistically adjusting and minimizing the energy of goodness-of-fit landscapes such as genetic algorithm (focusing on qualitatively optimizing the algorithm), neural network (preset or empirical algorithm focusing on optimizing a set of selected parameters for a selected neural patterns/circuits), and principal component analysis (statistical decompositions of components with maximum likelihood) could be used. FFT deconvolution also could be used to create a set of initial conditions for the said methods if necessary.

Analyte quantification: specific signal activity of a reporter needs to be known before being used for an assay (single intensity per unit amount of reporter particles or molecules). For surface binding, one reporter can be considered to represent one analyte. In solution binding, the relation between reporter and analyte needs to be determined experimentally. When a spectrum is collected, trained software as described previously is used to deconvolute the spectrum to determine the reporter concentration quantitatively. Based on reporters' specific activity and sample volume (surface area), multiple analytes can be quantified in a single assay.

Figure 9:
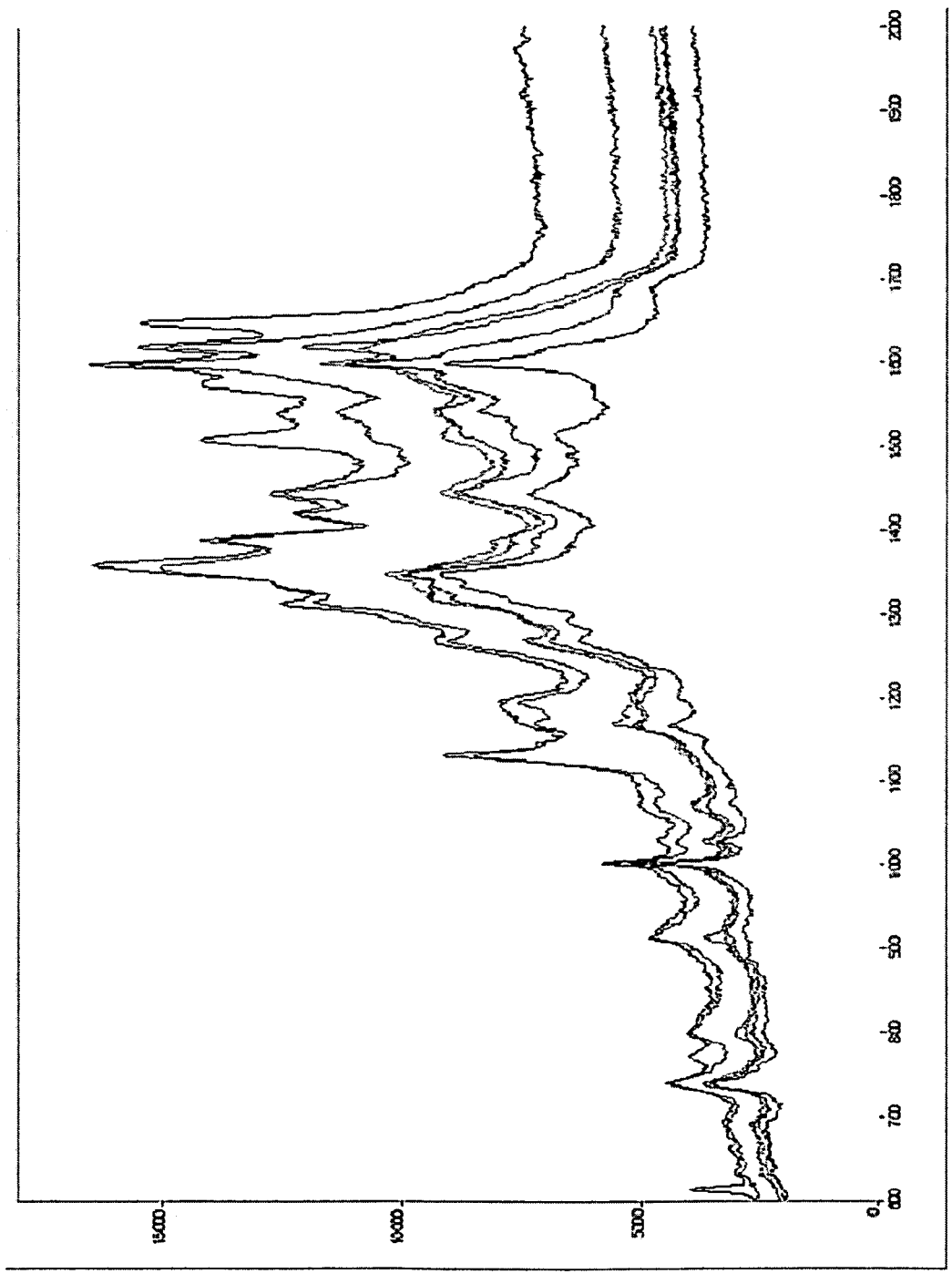
FIG. 9 shows Raman spectra of multiplexed COIN mixtures.

FIG. 9 shows the result of multiplexing seven COIN Tags. From bottom to the top, each plot in different color represents multiplexed COIN mixtures, starting from two COINs successively up to seven COINs in a same solution. In brief, each addition of new COIN introduces uniquely identifiable peaks on top of the existing peaks. General "finger printing" method such as the machine learning software with statistical software described above could be effectively used to identify and decompose the different signature components superimposed in the spectra of multiplex assay.

The embodiments of the invention could use silicon technology to fabricate interconnects for silicon chips to enable on-die synthesis of polymers such as DNA, peptides, and DNA-functionalized complementary nucleotide. Optionally, the embodiments of the invention could use wafer processing cluster tools (process instruments) for synthesis. Typically, in volume silicon processing, a manufacturing line has a cluster of instruments (several identical instruments). Each can support a process step or multiple process steps. By the embodiments of the invention, polymer synthesis can be treated as another process step in a device manufacturing line. A cluster of instruments can be configured within a facility to perform wafer level synthesis for efficient high volume manufacturing.

The devices of the embodiments of the invention may be formed by any suitable means of manufacture, including semiconductor manufacturing methods, microforming processes, molding methods, material deposition methods, etc., or any suitable combination of such methods. In certain embodiments one or more of the electrodes and/or the pad may be formed via semiconductor manufacturing methods on a semiconductor substrate. Thin film inorganic coatings may be selectively deposited on portions of the substrate and/or pad surface. Examples of suitable deposition techniques include vacuum sputtering, electron beam deposition, solution deposition, and chemical vapor deposition. The inorganic coatings may perform a variety of functions. For example, the coatings may be used to increase the hydrophilicity of a surface or to improve high temperature properties. Conductive coatings may be used to form electrodes. Coatings may be used to provide a physical barrier on the surface, e.g. to retain fluid at specific sites on the surface. The devices used in the present invention may be fabricated according to procedures well-known in the arts of microarray and semiconductor device manufacturing.

In some embodiments the probes may be selected from biomolecules, such as polypeptides, polynucleotides, glycoproteins, polysaccharides, hormones, growth factors, peptidoglycans, or the like. The probe could be natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. In embodiments employing oligonucleotide probes, the probes may be synthesized, in situ, on the surface of the pad in either the 3' to 5' or 5' to 3' direction using the 3'-β-cyanoethyl-phosphoramidites or 5'-β-cyanoethyl-phosphoramidites and related chemistries known in the art. In situ synthesis of the oligonucleotides may also be performed in the 5' to 3' direction using nucleotide coupling chemistries that utilize 3'-photoremovable protecting groups. Alternatively, the oligonucleotide probes may be synthesized on the standard controlled pore glass (CPG) in the 3' to 5' direction using 3'-β-cyanoethyl-phosphoramidites and related chemistries and incorporating a primary amine or thiol functional group onto the 5' terminus of the oligonucleotide. The oligonucleotides may then be covalently attached to the pad surface via their 5' termini using thiol or amine-dependent coupling chemistries known in the art. The density of the probes on the surface can range from about 1,000 to 200,000 probe molecules per square micron. The probe density can be controlled by adjusting the density of the reactive groups on the surface of the pad for either the in situ synthesis or post-synthesis deposition methods. Other suitable means for synthesis of probe as are known in the art may be employed.

The oligonucleotide probes include, but are not limited to, the four natural deoxyribonucleotides; deoxythymidylic acid, deoxycytidylic acid, deoxyadenylic acid and deoxyguanylic acid. The probes can also be ribonucleotides, uridylic acid, cytidylic acid, adenylic acid, and guanylic acid. Modified nucleosides may also be incorporated into the oligonucleotide probes. These include but are not limited to; 2'-deoxy-5-methylcytidine, 2'-deoxy-5-fluorocytidine, 2'-deoxy-5-iodocytidine, 2'-deoxy-5-fluorouridine, 2'-deoxy-5-iodouridine, 2'-O-methyl-5-fluorouridine, 2'-deoxy-5-iodouridine, 2'-deoxy-5(1-propynyl)uridine, 2'-O-methyl-5(1-propynyl)uridine, 2-thiothymidine, 4-thiothymidine, 2'-deoxy-5(1-propynyl)cytidine, 2'-O-methyl-5(1-propynyl)cytidine, 2'-O-methyladenosine, 2'-deoxy-2,6-diaminopurine, 2'-O-methyl-2,6-diaminopurine, 2'-deoxy-7-deazadenosine, 2'-deoxy-6methyladenosine, 2'-deoxy-8-oxoadenosine, 2'-O-methylguanosine, 2'-deoxy-7-deazaguanosine, 2'-deoxy-8-oxoguanosine, 2'-deoxyinosine or the like.

The polynucleotide probes can vary in length from a range of about 5 to about 100 nucleotides, such as about 8 to about 80 nucleotides, such as about 10 to about 60 nucleotides, and such as about 15 to about 50 nucleotides. Longer polynucleotide probes are typically employed for applications where the sample contains a high sequence-complexity target mixture. Shorter polynucleotide probes are typically employed in applications where single nucleotide discrimination, such as mutation detection, is desired.

The target molecule could be a nucleic acid such as genomic DNA, genomic RNA, messenger RNA, ribosomal RNA or transfer RNA, an oligonucleotide or polynucleotide of DNA or RNA generated by enzymatic process such as PCR or reverse transcription, or any synthetic DNA, RNA, or any other desired nucleic acid or any combination thereof. The target molecule may be double stranded or single stranded. It is preferred that the target molecule be single stranded in order to increase the efficiency of its interaction with the probe sequences. The target molecule could contain nanomaterials such a carbon nanotube, wherein the nanomaterial such as the carbon nanotube could be functionalized at its ends to molecules containing nucleic acid.

The architecture of the array probes may be either generic or specific with regard to the complementary target sequences that it may hybridize with. For example, an array of all possible 7-mer probe sequences could be used to interrogate targets having any sequence. The advantage of such an array is that it is not application specific and therefore generic. Alternatively, the probe array may contain polynucleotide sequences that are complementary to a specific target sequence or set of target sequences and individual or multiple mutations thereof. Such an array is useful in the diagnosis of specific disorders, which are characterized by the presence of a particular nucleic acid sequence. For example, the target sequence may be that of a particular exogenous disease causing agent, e.g. human immunodeficiency virus, or alternatively the target sequence may be that portion of the human genome which is known to be mutated in instances of a particular disorder, e.g., sickle cell anemia or cystic fibrosis, or to a portion of a genome known to be associated with certain phenotypes, e.g., resistance to certain drugs, over-reactivity to certain drugs, or even susceptibility to side-effects of certain drugs.

In one embodiment of the present invention, polymers on a plurality of dies on a wafer substrate are functionalized on the electrodes as follows. First, a terminal end of a monomer, nucleotide, or linker molecule (i.e., a molecule which "links," for example, a monomer or nucleotide to a substrate) is provided with at least one reactive functional group, which is protected with a protecting group removable by an electrochemically generated reagent. The protecting group(s) is exposed to reagents electrochemically generated at the electrode and removed from the monomer, nucleotide or linker molecule in a first selected region to expose a reactive functional group. The substrate is then contacted with the monomer or a pre-formed molecule (called the first molecule) such that the surface bonds with the exposed functional group(s) of the monomer or the pre-formed molecule. The first molecule may also bear at least one protected chemical functional group removable by an electrochemically generated reagent. The monomer or pre-formed molecule can then be deprotected in the same manner to yield a second reactive chemical functional group. A different monomer or preformed molecule (called the second molecule), which may also bear at least one protecting group removable by an electrochemically generated reagent, is subsequently brought in the vicinity of the substrate to bond with the second exposed functional group of the first molecule. Any unreacted functional group can optionally be capped at any point during the synthesis process. The deprotection and bonding steps can be repeated sequentially at the plurality of the predefined regions on the substrate until polymers or oligonucleotides of a desired sequence and length are obtained.

In another embodiment of the present invention, polymers on a plurality of dies on a wafer substrate are functionalized on the electrodes as follows. First, a substrate of a wafer having one or more molecules bearing at least one protected chemical functional group bonded on an array of electrodes on a plurality of dies is obtained. The array of electrodes is contacted with a buffering or scavenging solution. Following application of an electric potential to selected electrodes in the array of electrodes sufficient to generate electrochemical reagents capable of deprotecting the protected chemical functional groups, molecules on the array of electrodes are deprotected to expose reactive functional groups, thereby preparing them for bonding. A monomer solution or a pre-formed molecule (called the first molecule), such as proteins, nucleic acids, polysaccharides, and porphyrins, is then contacted with the substrate surface of the wafer and the monomers or pre-formed molecules are bonded in parallel with a plurality of deprotected chemical functional groups on a plurality of dies on the wafer. Another sufficient potential is subsequently applied to select electrodes in the array to deprotect at least one chemical functional group on the bonded molecule or another of the molecules bearing at least one protected chemical functional group on a plurality of dies on the wafer. A different monomer or pre-formed molecule (called the second molecule) having at least one protected chemical functional group is subsequently attached to a deprotected chemical functional group of the bonded molecule or the other deprotected molecule located at a plurality of dies of the wafer. The selective deprotection and bonding steps can be repeated sequentially until polymers or oligonucleotides of a desired sequence and length are obtained. The selective deprotection step is repeated by applying another potential sufficient to effect deprotection of a chemical functional group on a bonded protected monomer or a bonded protected molecule. The subsequent bonding of an additional monomer or pre-formed molecule to the deprotected chemical functional group(s) until at least two separate polymers or oligonucleotides of desired length are formed on the substrate.

Some of the advantages of the embodiments of the invention include:
Fast data collection, e.g., in array-based assays, one spectrum contain multiple data points; and in fluidic-based assays, magnetic force-assisted detection concentrated the analyte-probe complex, reducing scanning time)
High throughput (multiple tests can be performed at the same time in multiplexed analysis).
Use of small sample volume (crucial to clinical diagnosis)
Low cost (Less samples, reagents, and labor).

This embodiment of the invention relate to generating multiplex data and analyzing the resulting data. The embodiments of the invention can be used to collect information from multiple binding complexes in a single measurement (1 data integration time, for example 0.1 second); normally a separation step is used before any detection (for example, magnetic separation, centrifugation, etc.). The embodiments of the invention are different from current methods which uses beads, which are likely to be much larger than COINs and rely on a correlation between the fluorescence of the classification laser and the fluorescence of the reporter to detect a single type of binding complexes, while the COIN-based assay of some of the embodiments of the invention does not need this type of statistical correlation method because the label/tag signatures of COINs are directly read by Raman system.

The embodiments of the invention can be used to carry out the electrochemical syntheses of polymers such as DNA and peptides according to any of a variety of approaches known to person skilled in the art. For example, any of a variety of reduction/oxidation (redox) reactions may be employed to electrochemically control the localization and pH of a solution on Si-based electrodes to enable the attachment and elongation of polymers. In such methods, the electrical current drives the oxidation of an appropriate molecule at the anode(s) and the reduction of another molecule at the cathode (s) to control the kinetics and stoichiometry of acid-catalyzed organic syntheses on a Si-based circuit Such methods can also be used to generate high pH (basic) solutions, and to drive any other electrochemical redox reactions known to one skilled in the art that may or may not result in pH changes (e.g., can also be used to generate reactive free radicals).

Another embodiment of the invention is electrochemical detection using the array chip. Typically these methods employ measurements of current flow across a DNA monolayer tethered to a circuit on a silicon substrate. Current flow properties proportionately change when the DNA monolayers are bound by an appropriate redox molecule-tagged test DNA or untagged DNA that is co-added with a redox-active molecule that specifically binds double stranded DNA. Enzyme amplification methods can also be incorporated into such assays in order to enhance the electrochemical signal generated by binding events. Note that these methods can also be adapted by one skilled in the art to measure the binding between other molecular species such as between two proteins or a protein and a small molecule.

The array chip could also be used for therapeutic materials development, i.e., for drug development and for biomaterial studies, as well as for biomedical research, analytical chemistry, high throughput compound screening, and bioprocess monitoring. An exemplary application includes applications in which various known ligands for particular receptors can be placed on the array chip and hybridization could be performed between the ligands and labeled receptors.

Yet another application of the array chip of an embodiment of this invention includes, for example, sequencing genomic DNA by the technique of sequencing by hybridization. Non-biological applications are also contemplated, and include the production of organic materials with varying levels of doping for use, for example, in semiconductor devices. Other examples of non-biological uses include anticorrosives, antifoulants, and paints.

It is specifically contemplated that the array chip and/or the methods of manufacturing the array chip of an embodiment of the invention could be used for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis. Materials for these or other utilities may be formed proximate to one or a plurality of the electrodes in parallel on a plurality of dies of a silicon wafer, for example. Alternatively, materials may be formed by modifying the surface of one or a plurality of electrodes on a plurality of dies by generating reagents electrochemically.

It is further contemplated that an array chip of the embodiments of the invention could be used to develop screening methods for testing materials. That is, reagents electrochemically generated by an electrode on a die could be used to test the physical and chemical properties of materials proximate to the electrode. For example, the array chip could be used for testing corrosion resistance, electroplating efficiency, chemical kinetics, superconductivity, electro-chemiluminescence and catalyst lifetimes.

The advantageous characteristics of some of the embodiments of the invention are illustrated in the examples, which are intended to be merely exemplary of the invention.

The array chips of the embodiments of the invention are preferably silicon bio-chips built by using silicon process technology and SRAM like architecture with circuitries including electrode arrays, decoders, serial-peripheral interface, on chip amplification, for example.

The embodiments of this invention have several practical uses. For example, one embodiment of the invention allows molecules and nanomaterials detection/analysis based on the electrical readout of specific binding events (target to functionalized electrodes with probes) using CMOS-based devices. Another embodiment of the invention has potential applications for nanomaterials study (for example, in-situ analysis of DNA-mediated assembly of carbon nano-tubes on functionalized electrodes) to be used in electronic devices (CNT transistors and interconnects) as well as well as for detection of bio-species (DNA, protein, viruses etc.) for molecular diagnostics, homeland security, drug discovery and life science R&D work. Yet another embodiment of the invention could be to use Nanomaterials, such as carbon-nanotubes, in potential applications as interconnect materials. Carbon-nanotubes have lower resistivity than Cu and higher electromigration resistance (1000× higher than Cu). Yet another application could be to develop DNA functionalized electrodes with CMOS circuitry for immobilizing, detection, addressing, electrical readout and amplification of the signal can find potential application in silicon DNA chips. Silicon chips with DNA functionalized electrodes could find potential application to build nano-structures and in-situ assembly study of nanomaterials. Silicon DNA chips could also find potential application in medical diagnostics, homeland security devices, drug discovery and life science R&D work.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device for data collection comprising a beam emitter, a microfluidic channel (MFC), having an array of spots, a spectrometer, a detector; wherein the device has an ability to detect a binding complex comprising a first binding partner, a first reporter associated with the first binding partner, an analyte, a second binding partner, and a second reporter associated with the second binding partner, wherein the first reporter or the second reporter comprises a nanomaterial having more than 50% by weight of inorganic content, wherein the MFC comprises a microcoil or a Micro-Electro-Mechanical System (MEMS) device.

2. A device for data collection comprising a beam emitter, a chamber to hold a microarray, a spectrometer and a detector: wherein the device has an ability to detect a binding complex comprising a first binding partner, a first reporter associated with the first binding partner, an analyte, a second binding partner, and a second reporter associated with the second binding partner, wherein the first reporter or the second reporter comprises a nanomaterial having more than 50% by weight of inorganic content, wherein the chamber comprises an optical switch to detect the beam transmitted through the microarray.

3. The device of claim 2, wherein the spectrometer is a waveguide based spectrometer to detect a phase shift of a Raman signal emitted by the sample.

4. The device of claim 3, wherein the detector is to detect at least a characteristic of the Raman signal emitted by the sample.

5. The device of claim 4, further comprising a microprocessor comprising software or a hardware to identify the Raman signal.

6. The device of claim 1, wherein the MFC comprises an inorganic support and an optically transparent cover.

7. The device of claim 1, further comprising an analyte attached to at least one of the immobilized binding partner and another binding partner attached to the analyte and a reporter.

8. The device of claim 1, wherein the beam emitter is to emit a beam comprising laser.

9. The device of claim 1, further comprising an optical waveguide between the beam emitter and the MFC.

10. The device of claim 1, wherein the MFC comprises a detection site to illuminate a sample comprising a reporter attached to an analyte.

11. The device of claim 1, wherein the spectrometer is a waveguide based spectrometer to create a phase shift in a Raman signal emitted by the sample.

12. The device of claim 1, wherein the detector is to detect at least a characteristic of a Raman signal emitted by the sample.

13. The device of claim 1, further comprising a microprocessor comprising software or a hardware to identify the Raman signal.

14. The device of claim 1, wherein the MFC comprises a plurality of first binding partners immobilized on spots in the MFC.

15. The device of claim 1, wherein the MFC further comprises a plurality of COINs or magnetic COINs immobilized on spots.

16. The device of claim 2, wherein the spectrometer is a waveguide based spectrometer to detect a phase shift of a Raman signal emitted by the sample.

17. The device of claim 2, wherein the detector is to detect at least a characteristic of a Raman signal emitted by the sample.

18. The device of claim 2, further comprising a microprocessor comprising software or a hardware to identify a Raman signal.

19. The device of claim 2, wherein the microarray comprises a plurality of first binding partners immobilized on spots on the microarray.

20. The device of claim 2, wherein the microarray further comprises a plurality of COINs immobilized on spots.

21. The device of claim 2, wherein the plurality of COINs comprise a magnetic COIN.

* * * * *